United States Patent [19]

Klintworth, Jr.

[11] Patent Number: 4,934,356

[45] Date of Patent: Jun. 19, 1990

[54] WATER-ACTIVATED ORTHOPEDIC CAST COMPOSITION HAVING COLORANT

[75] Inventor: William G. Klintworth, Jr., Tulsa, Okla.

[73] Assignee: Carapace Incorporated, Tulsa, Okla.

[21] Appl. No.: 4,087

[22] Filed: Jan. 15, 1987

[51] Int. Cl.$^5$ .................... A61F 13/04; A61L 15/10; A61L 15/14

[52] U.S. Cl. ................................... 128/90; 427/342; 427/389.8; 428/253; 428/254; 428/255; 428/273; 428/425.6; 428/913

[58] Field of Search ................. 128/90; 428/253, 254, 428/255, 273, 542.8, 913

[56] References Cited

U.S. PATENT DOCUMENTS

| | | | |
|---|---|---|---|
| 4,316,457 | 2/1982 | Liegeois | 128/89 R |
| 4,376,438 | 3/1983 | Straube et al. | 128/90 |
| 4,574,793 | 3/1986 | Lee et al. | 128/90 |
| 4,652,493 | 3/1987 | Reichmann et al. | 128/90 |

FOREIGN PATENT DOCUMENTS 2651089  6/1980  Fed. Rep. of Germany .

*Primary Examiner*—James C. Cannon
*Attorney, Agent, or Firm*—Head & Johnson

[57] ABSTRACT

An orthopedic cast forming composition which is coated upon a flexible fabric as a water-curable prepolymer resin wherein the resin is formed by the reaction of an isocyanate and a polyol wherein the polyol has a colorant premixed therewith.

14 Claims, No Drawings

WATER-ACTIVATED ORTHOPEDIC CAST COMPOSITION HAVING COLORANT

FIELD OF THE INVENTION

The invention disclosed herein relates to orthopedic bandages comprising a cast forming composition that is used in the preparation of surgical casts designed to immobilize and support portions of the body, e.g. a leg, arm, wrist, neck and the like. The improvement herein relates to a composition coated upon a flexible fabric which when set will be of a color other than natural white. The material broadly comprises a substrata and a reactive component system which hardens upon exposure to air by reaction with moisture.

BACKGROUND

For many years orthopedic surgeons and other specialists have long worked with Plaster of Paris, for many years almost exclusively, in the preparation of surgical casts. The problems associated with Plaster of Paris as to weight, water damage, x-ray opaqueness etc. are well documented. Recently Plaster of Paris has to a large extent been replaced with the development of orthopedic bandages which utilize cast forming compositions and mixtures using water soluble vinyl monomers such as those selected from the group consisting of diacetone acrylamide (DAA), N-isopropylacrylamide (N-IPA) and mixtures thereof wherein the monomers are polymerizable in the presence of water by means of an amine catalyst or a redox catalyst system that comprises an oxidation component and a reducing agent. Such an orthopedic bandage is described in U.S. Pat. No. 3,630,194. The bandages are hardened in a manner similar to the Plaster of Paris bandages by dipping the bandage into tap water which is then formed about the portion of the body to be immobilized or supported. Other prior art orthopedic bandages are found in U.S. Pat. Nos. 4,411,262; 4,376,438; 4,344,423; 4,502,479; and 4,433,680. The resulting hardened bandage has always been of a natural (white) color which is subject to discoloration becoming unsightly and without any fashionable character. The addition of a colorant to the cast material must take into due consideration the effect of the colorant to the cast forming material, its reactiveness, its strength, its shelf life, and possible reaction to the patient. Also, the formation of a homogeneous solution of the polymer must consider the chemical effects involved so as not to radically change the composition or the reactions involved.

SUMMARY OF THE INVENTION

The invention herein relates to and has for its object to provide a novel orthopedic bandage wherein the resultant hardened cast is of a color other than natural (white) which occurs as a result of the prior art methods and composition.

The invention also has for its object to provide a novel method of forming a polymer orthopedic cast composition which is to be coated upon a flexible fabric and in particular to a method of mixing a colorant with the composition. In particular, the composition being a water-curable prepolymer resin that is formed by the reaction of an isocyanate and a polyol wherein the polyol is premixed with a colorant such as pink or blue. In use the components of the composition are such that an orthopedic surgeon or specialist need only dip the bandage in water in order to initiate polymerization and prepare the bandage for use.

Another object of the invention is to provide a method of pre-preparation of a polypropylene oxide colored polyol for use as a part of a water-cured polyisocyanate prepolymer orthopedic cast resin. The steps of the method comprise first separating a minor portion of the polyol from the total batch of the polyol. A colorant is slowly added and mixed with the minor portion of the polyol. The minor portion may be heated and mixing continued until the colorant has dissolved in the minor portion. Thereafter, the minor portion of colored polyol is added and mixed with the remaining major batch of said polyol which is thereafter added to and mixed with said isocyanate.

The resulting invention provides an orthopedic cast of attractive fashionable color that does not interfere with the shelf life of the unpolymerized composition or interfere with the high strength characteristics of the cast composition, or create side effects upon the patient.

According to the preferred embodiment of the present invention, the resin composition is comprised of two parts, premix "A" that is reacted with premix "B". Premix "A" is comprised of an isocyanate resin such as that sold by Upjohn Company under the registered trademark "Isonate 143L," a foam suppressing material such as Union Carbide SAG-47, a silicone anti-foam compound, or Dow Corning DB-100 silicone fluid and a preservative or stabilizer such as benzoyl chloride to prolong shelf life.

Premix "B" is comprised of a polypropylene oxide polyol such as is available under the registered trademark "Pluracol P-710" from BASF Wyandotte, a catalyst such as Dimethylethanolamine (DMEA) and/or an amino/glycol mixture such as a material identified under the registered trademark Niax A-1 which is used to control the reactivity of the resin once it is exposed to water.

In the preparation of premix "A", the Isonate 143L is measured and put into a reaction vessel under vacuum. When the material has been totally added the vacuum is released and dry nitrogen is then purged into the reaction vessel. While the reaction vessel is still being purged with dry nitrogen, the defoaming material is added and mixed into the Isonate 143L. Mixing continues for at least 10 minutes with the benzoyl chloride being slowly added to the vessel which is still being purged with the dry nitrogen and allowed to mix for at least 20 minutes. The purpose of the dry nitrogen being to prevent intrusion of moisture into the premix.

In preparing premix "B", a minor portion e.g., 10%, is separately removed while the remaining portion is added to a second reaction vessel. The aforesaid minor portion is then taken to a separate mixing vessel where the proper weight of a colorant is slowly added and mixed with the minor portion of poloyl. This mixture can be heated during mixing until, in any event, the colorant material has completely dissolved within the minor portion. Thereafter this solution is added to the second reaction vessel where a vacuum of 20 to 30 inches of mercury is applied and mixing begun for at least four hours. Once the Pluracol P-710 has been vacuum dried, the vacuum is released and the nitrogen is purged into the second reaction vessel. The addition of catalyst(s) in a measured amount is then added to the premix under the nitrogen purge and mixing continues for thirty minutes to insure a homogeneous solution.

With the premix "B" reaction vessel under a dry nitrogen purge, its contents are slowly added and mixed with premix "A" in its reaction vessel which is also under a dry nitrogen purge. The increments of addition are such that it takes 20-25 minutes total time. Once the addition is complete, the final mixing action should be continued for one to one and one-half hours under a dry nitrogen purge.

The resin used in the casting material may be any curable resin such as those described in the aforesaid prior art patents which will satisfy the functional requirements of an orthopedic cast such that the addition of a colorant material or non-functional additive to the resin will still maintain the characteristics of a desirable orthopedic cast that is not harmful to either the patient or the person applying the cast. In addition, the resin and the added colorant as specified in this invention must be sufficiently compatible to ensure rapid hardening of the cast yet permit sufficient working time to apply and shape the cast.

The preferred resins are those cured with water. A number of classes of water-curable resins known in the art are suitable, including polyurethanes, cyanoacrylate esters and, when combined with moisture sensitive catalysts, epoxy resins and prepolymers terminated at their ends with trialkoxy- or trihalo-silane groups. Other useful resins are polyethers, polyester, MDI, and TDI polymerics. Although there are other resin systems useful to the purposes of this invention that are cured by other than the use of water, the preferred resin is one that is water curable.

The resulting resin of the invention is coated onto a fabric. The preferred fabric being a knit fiberglass material within the preferred range of 250-280 mesh-size openings per square inch and preferably 265 openings per square inch. A typical knit fiberglass is that manufactured by MacMurray Fabrics, Inc. The structural strength and textural characteristics as to porosity and thickness are chosen to provide rapid and thorough mixing of the curing agent with the impregnated resin component. A fabric selected is to be thin with a high surface-to-volume ratio. The fabric used is formed in rolls of various widths generally from one to six inches wide and is impregnated with the curable resin material by an environmentally controlled process to eliminate moisture which would otherwise cause the premature hardening and/or low shelf life of the resulting impregnated fabric. The amount of the resin component is controlled such that there is sufficient formation of a strong inter-layer laminate bond but yet will not occlude the porosity and unnecessarily thicken the film and the fabric. The resulting resin coated fabric is formed in a roll wound up on a plastic core and then packaged within an hermetically sealed container. When it is ready for use, the package is opened and the roll is fully immersed in water for sufficient time for the water to seep into the porous material and displace the air. The roll is then unwound during the formation and wrapping of the cast in a manner well known to the orthopedic surgeon or specialist.

Although the preferred colorants are pink and blue, it is to be understood that other colors are inclusive of use in this invention. Preferably, a blue colorant is formed of a combination of Orasol Blue GN in combination with Orasol Pink 5BLG which are manufactured and sold under those trademarks by Ciba-Geigy. The concentrations are within the ranges of 0.001% to 5.0%, preferably 0.07% by weight of the blue, and within the ranges of 0.001% to 5.0%, preferably 0.007% by weight of pink. A pink coloring is formed by Orasol Pink 5BLG, a monoazo chrome complex, manufactured and sold under that trademark by Ciba-Geigy. The concentration used in the invention is 0.01% by weight.

What is claimed:

1. An orthopedic cast forming composition for immobilizing a patient's body or portions thereof, said composition comprising a flexible fabric having coated thereon a water-curable prepolymer resin, said prepolymer being one produced by the reaction of an isocyanate with a polyol into which a colorant had been mixed prior to said reaction, said colorant being non-reactive to said patient.

2. The composition of claim 1 wherein said fabric is a knit fiberglass of mesh size within the range of 250-280 openings per square inch.

3. The composition of claim 1 wherein said fabric is fiberglass of mesh size having 265 openings per square inch.

4. The composition of claim 1 wherein said colorant is blue.

5. The composition of claim 4 where said colorant is formed of 0.07% by weight of blue colorant and 0.007% by weight of pink colorant.

6. The composition of claim 1 wherein said colorant is pink.

7. The composition of claim 6 wherein said colorant is pink in concentration of 0.01% by weight.

8. A colored orthopedic cast-forming composition for immobilizing a patient's body or portions thereof, said composition comprising a flexible fabric having coated thereon a water-curable prepolymer resin formed by the reaction of one reactant with another reactant wherein the latter reactant was one with which a colorant had been intermixed prior to conducting said reaction, said colorant being one which is patient non-reactive and does not interfere with the shelf life and strength or rapid-hardening characteristics of the cast forming composition.

9. The composition of claim 8 wherein said fabric is a knit fiberglass of mesh size within the range of 250-280 openings per square inch.

10. The composition of claim 8 wherein said fabric is fiberglass of mesh size having 265 openings per square inch.

11. The composition of claim 8 wherein said colorant is blue.

12. The composition of claim 11 where said colorant is formed of 0.07% by weight of blue colorant and 0.007% by weight of pink colorant.

13. The composition of claim 8 wherein said colorant is pink.

14. The composition of claim 13 wherein said colorant is pink in concentration of 0.01% by weight.

* * * * *